(12) United States Patent
Matsumoto et al.

(10) Patent No.: US 12,357,264 B2
(45) Date of Patent: Jul. 15, 2025

(54) WHEEZING DETECTION DEVICE AND WHEEZING DETECTION PROGRAM

(71) Applicant: OMRON HEALTHCARE CO., LTD., Muko (JP)

(72) Inventors: Naoki Matsumoto, Kyoto (JP); Kenji Hashino, Kyoto (JP); Kei Asai, Kyoto (JP); Naoto Ohgami, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 846 days.

(21) Appl. No.: 17/105,685

(22) Filed: Nov. 27, 2020

(65) Prior Publication Data

US 2021/0077056 A1 Mar. 18, 2021

Related U.S. Application Data

(63) Continuation of application No. PCT/JP2019/019180, filed on May 14, 2019.

(30) Foreign Application Priority Data

May 30, 2018 (JP) .................................. 2018-103860

(51) Int. Cl.
*A61B 7/00* (2006.01)
*A61B 7/04* (2006.01)

(52) U.S. Cl.
CPC ................ *A61B 7/003* (2013.01); *A61B 7/04* (2013.01)

(58) Field of Classification Search
CPC ....... A61B 7/003; A61B 7/04; A61B 5/02416; A61B 7/00; A61B 5/0826; A61B 5/0823; A61B 5/091; A61B 2017/00809
See application file for complete search history.

(56) References Cited

U.S. PATENT DOCUMENTS 8,827,920 B2 * 9/2014 Lee ...................... A61B 5/742
600/528
8,956,305 B2 * 2/2015 Trice ...................... A61B 7/04
600/528

(Continued)

FOREIGN PATENT DOCUMENTS

CN  104605886 A   5/2015
CN  105208921 A   12/2015

(Continued)

OTHER PUBLICATIONS

Official Communication issued in corresponding Chinese Patent Application No. 201980036454.5, mailed on Dec. 30, 2021.

(Continued)

*Primary Examiner* — Patrick Fernandes
(74) *Attorney, Agent, or Firm* — Keating & Bennett, LLP

(57) ABSTRACT

There is provided a wheezing detection device, including: a wheezing determiner that performs processing of determining whether wheezing is included in the pulmonary sound of the subject, based on the signal of the pulmonary sound that is measured by a sound measurer after an instruction for starting wheezing detection processing is issued; and a controller that ends measurement of the signal of the pulmonary sound performed by the sound measurer and reports a result of the processing, in a case where an elapsed time period from a measurement start time point of the signal, which is firstly measured by the sound measurer after the instruction is issued, reaches a predetermined time period set in advance, or in a case where it is determined by the wheezing determiner that wheezing is included in the pulmonary sound of the subject.

12 Claims, 9 Drawing Sheets

(56) References Cited

U.S. PATENT DOCUMENTS

| | | |
|---|---|---|
| 2002/0058889 A1 | 5/2002 | Lee |
| 2006/0077063 A1* | 4/2006 | Cheng .................... A61B 7/003 340/573.1 |
| 2007/0118301 A1* | 5/2007 | Andarawis .............. G01M 5/00 702/33 |
| 2007/0185390 A1* | 8/2007 | Perkins ................. A61B 5/318 600/300 |
| 2009/0312638 A1* | 12/2009 | Bartlett ................ A61B 8/4427 600/443 |
| 2012/0123226 A1* | 5/2012 | Schwenk ............. A61B 5/1123 600/595 |
| 2012/0203491 A1* | 8/2012 | Sun .................. H04W 52/0219 702/108 |
| 2013/0060100 A1* | 3/2013 | Wurm .................... A61B 7/003 600/301 |
| 2014/0276167 A1 | 9/2014 | Dasgupta et al. |
| 2016/0166210 A1* | 6/2016 | Al-Ali ................ A61B 5/02416 600/323 |
| 2017/0325777 A1 | 11/2017 | Asai |
| 2017/0332993 A1 | 11/2017 | Asai |
| 2018/0206763 A1 | 7/2018 | Cao et al. |
| 2019/0209094 A1 | 7/2019 | Dasgupta et al. |

FOREIGN PATENT DOCUMENTS

| | | |
|---|---|---|
| CN | 105232049 A | 1/2016 |
| JP | 2002-165789 A | 6/2002 |
| JP | 2016-158806 A | 9/2016 |
| JP | 2016-158807 A | 9/2016 |
| TW | 200611678 A | 4/2006 |
| WO | 01/19243 A1 | 3/2001 |
| WO | 2016/166318 A1 | 10/2016 |

OTHER PUBLICATIONS

Official Communication issued in International Patent Application No. PCT/JP2019/019180, mailed on Aug. 6, 2019.

\* cited by examiner

WHEEZING DETECTION DEVICE AND WHEEZING DETECTION PROGRAM

CROSS-REFERENCE TO RELATED APPLICATIONS

This application is a continuation of PCT application No. PCT/JP2019/019180, which was filed on May 14, 2019 based on Japanese Patent Application No. 2018-103860 filed on May 30, 2018, the contents of which are incorporated herein by way of reference.

BACKGROUND

The present invention relates to a wheezing detection device and a wheezing detection program.

A device has been known that can utilize a microphone to extract pulmonary sounds as electrical signals. Pulmonary sounds are all sounds that are generated with respiratory movements in the lungs and the chest, regardless of whether being normal or abnormal, except for sounds originating from the cardiovascular system. The pulmonary sound is classified into a respiratory sound, which is a physiological sound originating from an air flow generated in the airway due to respiration, and an adventitious sound that is an abnormal sound such as wheezing or pleural friction rub, which is generated in pathological conditions.

For example, Patent Literature 1 discloses a device capable of displaying a time course of occurrence frequency of wheezing in a subject.

Patent Literature 1: JP-A-2016-158807

Wheezing does not always occur frequently even when symptoms of asthma are poor. Therefore, it is desirable that measurement time for the pulmonary sound is as long as possible. However, for an ordinary user other than a medical professional, it is difficult to determine how long the measurement time for the pulmonary sound would be sufficient.

Further, in order to improve detection accuracy of wheezing, it is desirable that the subject is in a resting state (a state where he/she is not talking and a state where he/she is not moving) during the measurement of pulmonary sound. However, for example, in a case where the subject is an infant, it is difficult to maintain the subject in a resting state for a long time. Therefore, if wheezing is occurring at a high frequency, it is desirable to detect the wheezing at a timing as early as possible and terminate the use of the device.

Patent Literature 1 discloses that processing of determining presence or absence of wheezing is performed every unit time period of, for example, 30 seconds, 1 minute, 2 minutes, 5 minutes, 10 minutes, or 30 minutes. The device disclosed in Patent Literature 1 is worn by a subject for a period sufficiently longer than the unit time period, and continuously measures the pulmonary sound.

This device is useful for a doctor to grasp the symptoms of asthma of the subject in detail. However, when it is assumed that the device is used only to know whether a child in a family has wheezing so as to determine whether to take him/her to a hospital or determine whether to give him/her medicine, it is not necessary to measure the pulmonary sound over a long time period as described above.

SUMMARY

The present invention has been made in view of the above circumstances, and an object thereof is to provide a wheezing detection device and a wheezing detection program capable of shortening a time period to an end of use of the device in some cases while ensuring a sufficient amount of signal of the pulmonary sound to determine presence or absence of wheezing.

According to one aspect of the present invention, there is provided a wheezing detection device including: a sound measurer for measuring a signal of a pulmonary sound of a subject; a wheezing determiner that performs processing of determining whether wheezing is included in the pulmonary sound of the subject, based on the signal of the pulmonary sound that is measured by the sound measurer after an instruction for starting wheezing detection processing is issued; and a controller that ends measurement of the signal of the pulmonary sound performed by the sound measurer and reports a result of the processing, in a case where an elapsed time period from a measurement start time point of the signal, which is firstly measured by the sound measurer after the instruction is issued, reaches a predetermined time period set in advance, or in a case where it is determined by the wheezing determiner that wheezing is included in the pulmonary sound of the subject.

According other aspect of the present invention, the wheezing detection device further includes: an invalid period determiner that determines whether the signal measured by the sound measurer is a specific signal possible to affect a result of the processing, and that when the signal is determined to be the specific signal, determines a period in which the signal is measured as an invalid period. The controller further ends the measurement of the signal of the pulmonary sound performed by the sound measurer and reports a state where determination of presence or absence of wheezing is not possible, in a case where total time of periods determined as the invalid period exceeds a predetermined threshold.

According to other aspect of the present invention, the predetermined time period is a time period selected from a range of 20 seconds or more and 60 seconds or less.

According to other aspect of the present invention, the predetermined time period is a time period selected from a range of 20 seconds or more and 40 seconds or less.

According to other aspect of the present invention, the threshold is a value of half of the predetermined time period.

According to other aspect of the present invention, the predetermined time period is a time period selected from a range of 10 seconds or more and 30 seconds or less.

According to other aspect of the present invention, there is provided a wheezing detection device including: a sound measurer for measuring a signal of a pulmonary sound of a subject; a wheezing determiner that performs processing of determining whether wheezing is included in the pulmonary sound of the subject, based on the signal of the pulmonary sound that is measured by the sound measurer after an instruction for starting wheezing detection processing is issued; a valid period determiner that determines whether the signal measured by the sound measurer is a specific signal possible to affect a result of the processing, and that when the signal is not determined to be the specific signal, determines a period in which the signal is measured as a valid period; and a controller that ends measurement of the signal of the pulmonary sound performed by the sound measurer and reports a result of the processing, in a case where total time of periods determined as the valid period after the instruction is issued reaches a predetermined time period set in advance, or in a case where it is determined by the wheezing determiner that wheezing is included in the pulmonary sound of the subject.

According to other aspect of the present invention, the predetermined time period is a time period selected from a range of 10 seconds or more and 30 seconds or less.

According to other aspect of the present invention, there is provided a wheezing detection device including: a sound measurer for measuring a signal of a pulmonary sound of a subject; a wheezing determiner that performs processing of determining whether wheezing is included in the pulmonary sound of the subject, based on the signal of the pulmonary sound that is measured by the sound measurer after an instruction for starting wheezing detection processing is issued; a valid period determiner that determines whether the signal measured by the sound measurer is a specific signal possible to affect a result of the processing, and that when the signal is not determined to be the specific signal, determines a period in which the signal is measured as a valid period; an invalid period determiner that determines whether the signal measured by the sound measurer is a specific signal possible to affect a result of the processing, and that when the signal is determined to be the specific signal, determines a period in which the signal is measured as an invalid period; and a controller that selectively performs one or two of a first control, a second control and a third control. The first control is control of ending measurement of the signal of the pulmonary sound performed by the sound measurer and reporting a result of the processing, in a case where an elapsed time period from a measurement start time point of the signal, which is firstly measured by the sound measurer after the instruction is issued, reaches a predetermined time period set in advance, or in a case where it is determined by the wheezing determiner that wheezing is included in the pulmonary sound of the subject. The third control is control of ending measurement of the signal of the pulmonary sound performed by the sound measurer and reporting a result of the processing, in a case where an elapsed time period from a measurement start time point of the signal, which is firstly measured by the sound measurer after the instruction is issued, reaches a predetermined time period set in advance, or in a case where it is determined by the wheezing determiner that wheezing is included in the pulmonary sound of the subject, and further ending the measurement of the signal of the pulmonary sound performed by the sound measurer and reporting a state where determination of presence or absence of wheezing is not possible, in a case where total time of periods determined as the invalid time period exceeds a predetermined threshold in a process in which the elapsed time period reaches the predetermined time period. The second control is control of ending measurement of the signal of the pulmonary sound performed by the sound measurer and reporting a result of the processing, in a case where total time of periods determined as the valid period after the instruction is issued reaches a predetermined time period set in advance, or in a case where it is determined by the wheezing determiner that wheezing is included in the pulmonary sound of the subject.

According to other aspect of the present invention, there is provided a storage medium which stores a wheezing detection program for causing a computer to execute: a wheezing determining step of performing processing of determining whether wheezing is included in a pulmonary sound of a subject, based on a signal of the pulmonary sound that is measured, by a sound measurer for measuring the signal of the pulmonary sound of the subject, after an instruction for starting wheezing detection processing is issued; and a control step of ending measurement of the signal of the pulmonary sound performed by the sound measurer and reporting a result of the processing, in a case where an elapsed time period from a measurement start time point of the signal, which is firstly measured by the sound measurer after the instruction is issued, reaches a predetermined time period set in advance, or in a case where it is determined through the wheezing determining step that wheezing is included in the pulmonary sound of the subject.

According to other aspect of the present invention, there is provided a storage medium which stores a wheezing detection program for causing a computer to execute: a wheezing determining step of performing processing of determining whether wheezing is included in a pulmonary sound of a subject, based on a signal of the pulmonary sound that is measured, by a sound measurer for measuring the signal of the pulmonary sound of the subject, after an instruction for starting wheezing detection processing is issued; a valid period determining step of determining whether the signal measured by the sound measurer is a specific signal possible to affect a result of the processing, and when the signal is not determined to be the specific signal, determining a period in which the signal is measured as a valid period; and a control step of ending measurement of the signal of the pulmonary sound performed by the sound measurer and reporting a result of the processing, in a case where total time of periods determined as the valid period after the instruction is issued reaches a predetermined time period set in advance, or in a case where it is determined through the wheezing determining step that wheezing is included in the pulmonary sound of the subject.

According to other aspect of the present invention, there is provided a storage medium which stores a wheezing detection program for causing a computer to execute: a wheezing determining step of performing processing of determining whether wheezing is included in a pulmonary sound of a subject, based on a signal of the pulmonary sound that is measured, by a sound measurer for measuring the signal of the pulmonary sound of the subject, after an instruction for starting wheezing detection processing is issued; a valid period determining step of determining whether the signal measured by the sound measurer is a specific signal possible to affect a result of the processing, and when the signal is not determined to be the specific signal, determining a period in which the signal is measured as a valid period; an invalid period determining step of determining whether the signal measured by the sound measurer is a specific signal possible to affect a result of the processing, and when the signal is determined to be the specific signal, determining a period in which the signal is measured as an invalid period; and a control step of selectively performing one or two of a first control, a second control and a third control. The first control is control of ending measurement of the signal of the pulmonary sound performed by the sound measurer and reporting a result of the processing, in a case where an elapsed time period from a measurement start time point of the signal, which is firstly measured by the sound measurer after the instruction is issued, reaches a predetermined time period set in advance, or in a case where it is determined through the wheezing determining step that wheezing is included in the pulmonary sound of the subject. The third control is control of ending measurement of the signal of the pulmonary sound performed by the sound measurer and reporting a result of the processing, in a case where an elapsed time period from a measurement start time point of the signal, which is firstly measured by the sound measurer after the instruction is issued, reaches a predetermined time period set in advance, or in a case where it is determined through the wheezing determining step that wheezing is included in the pulmonary sound of the subject, and further ending the measurement of the signal of the pulmonary sound performed by the sound measurer and reporting a state where determination of presence or absence of wheezing is not possible, in a case where total time of periods determined as the invalid time period exceeds a predetermined threshold in a process in which the elapsed time period reaches the predetermined time period. The second control is control of ending measurement of the signal of the pulmonary sound performed by the sound measurer and reporting a result of the processing, in a case where total time of periods determined as the valid period after the instruction is issued reaches a predetermined time period set in advance, or in a case where it is determined through the wheezing determining step that wheezing is included in the pulmonary sound of the subject.

DESCRIPTION OF EMBODIMENTS (Outline of Wheezing Detection Device of Embodiment)

First, an outline of an embodiment of a wheezing detection device of the present invention will be described. The wheezing detection device of the embodiment measures a pulmonary sound from a human body, and when it is determined that wheezing is included in a measurement sound, reports that. In this way, support is given in determination of whether to give medicine to the subject, or determination of whether to bring the subject to a hospital.

The wheezing detection device includes a sound measurer (first sound measuring instrument M1 to be described later) for measuring a pulmonary sound, and after a wheezing detection instruction is issued, determines presence or absence of wheezing based on a signal of the pulmonary sound measured by the sound measurer. In a case where it is determined that wheezing is included in the pulmonary sound, or in a case where an elapsed time period from a measurement start time point at which pulmonary sound measurement is started reaches a predetermined time period (predetermined time period T1 to be described later) that is determined in advance and that is necessary for determination of presence or absence of wheezing, the wheezing detection device ends the pulmonary sound measurement performed by the sound measurer and reports a result of the determination of presence or absence of wheezing.

In a case of a subject in which wheezing is frequently occurring, with such an operation, it is possible to know early that wheezing has occurred, and it is possible to improve convenience. In addition, the subject does not have to be kept at rest for a long time, and the burden on both the subject and a user can be reduced. Further, the pulmonary sound measurement can be terminated early, and power consumption can be reduced.

When the elapsed time period from a measurement start time point reaches the predetermined time period, the pulmonary sound measurement is terminated, and the result of the determination of presence or absence of wheezing is reported. Since the predetermined time period is, for example, a time period necessary for determining presence or absence of wheezing, when it is not determined that there is wheezing until the elapsed time period reaches the predetermined time period, it is possible to accumulate signals of the pulmonary sounds with sufficient time in the device, and to obtain a result of presence or absence of wheezing with high reliability. The user may only continue the use of the device until the result is reported without paying particular attention to the predetermined time period. Therefore, the convenience of the device can be improved.

Hereinafter, a specific configuration example of the wheezing detection device of the embodiment will be described.

Embodiment

Figure 1:
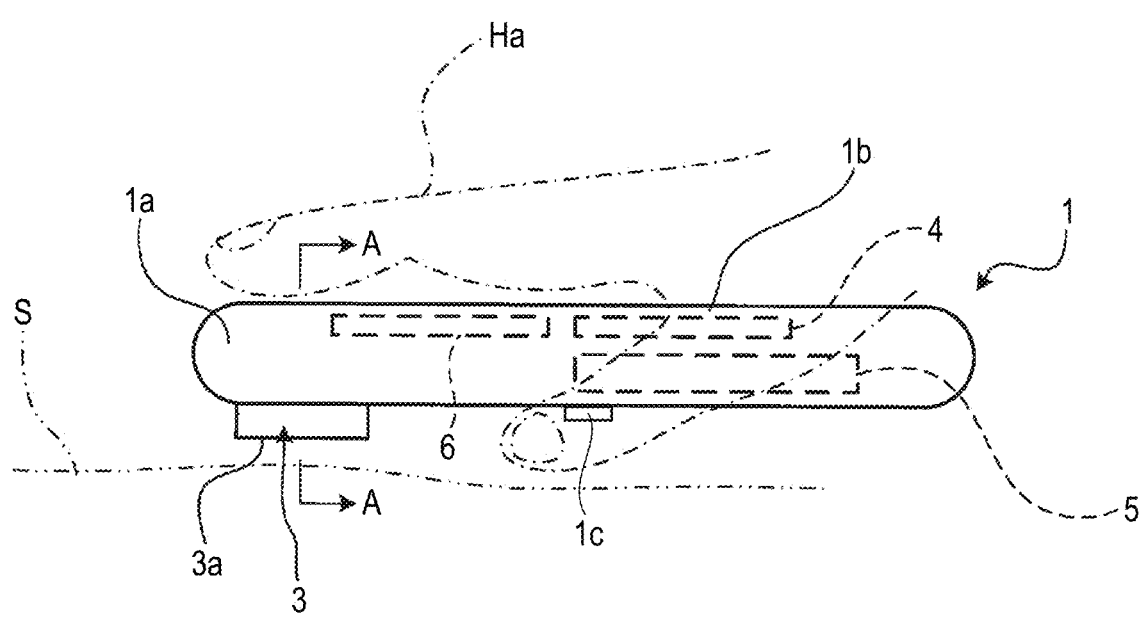
FIG. 1 is a side view illustrating a schematic configuration example of a wheezing detection device 1 as an embodiment of a wheezing detection device of the present invention.

FIG. 1 is a side view illustrating a schematic configuration example of a wheezing detection device 1 as an embodiment of a wheezing detection device of the present invention. As illustrated in FIG. 1, the wheezing detection device 1 has a rod-like grip portion 1b formed of a housing made of resin, metal, or the like, and on one end side of the grip portion 1b, a head portion 1a is provided.

Inside the grip portion 1b, an integrated controller 4 that performs integral control of the whole wheezing detection device 1, a battery 5 that supplies a voltage required for operation, and a display unit 6 that displays an image by a liquid crystal display panel, an organic electro luminescence (EL) display panel or the like are provided.

The integrated controller 4 includes various processors, a random access memory (RAM), a read only memory (ROM), and the like, and controls each piece of hardware of the wheezing detection device 1 in accordance with a program. In the ROM of the integrated controller 4, programs including a wheezing detection program are stored.

The various processors include a central processing unit (CPU) that is a general-purpose processor that executes programs to perform various types of processing, a programmable logic device (PLD) that is a processor whose circuit configuration can be changed after manufacture of an field programmable gate array (FPGA) or the like, a dedicated electric circuit that is a processor having a circuit configuration designed for executing specific processing such as an application specific integrated circuit (ASIC) or the like, and the like.

More specifically, structures of these various processors are electric circuits in which circuit elements such as semiconductor elements are combined.

The integrated controller 4 may be configured with one of the various processors, or may be configured with a combination of two or more processors of the same type or different types (for example, a combination of a plurality of FPGAs or a combination of a CPU and an FPGA).

The head portion 1a is provided with a measurer 3 protruding toward one side (a lower side in FIG. 1) in a direction substantially orthogonal to a longitudinal direction of the grip portion 1b. At a tip end of the measurer 3, a pressure receiving portion 3a that is to be brought into contact with a body surface S of a living body, which is a subject, to receive a pressure from the body surface S is provided.

In using the wheezing detection device 1, a user places, for example, an index finger of his/her hand Ha on a back surface of the measurer 3 in the head portion 1a, and presses the pressure receiving portion 3a of the measurer 3 against the body surface S with the index finger.

Figure 2:
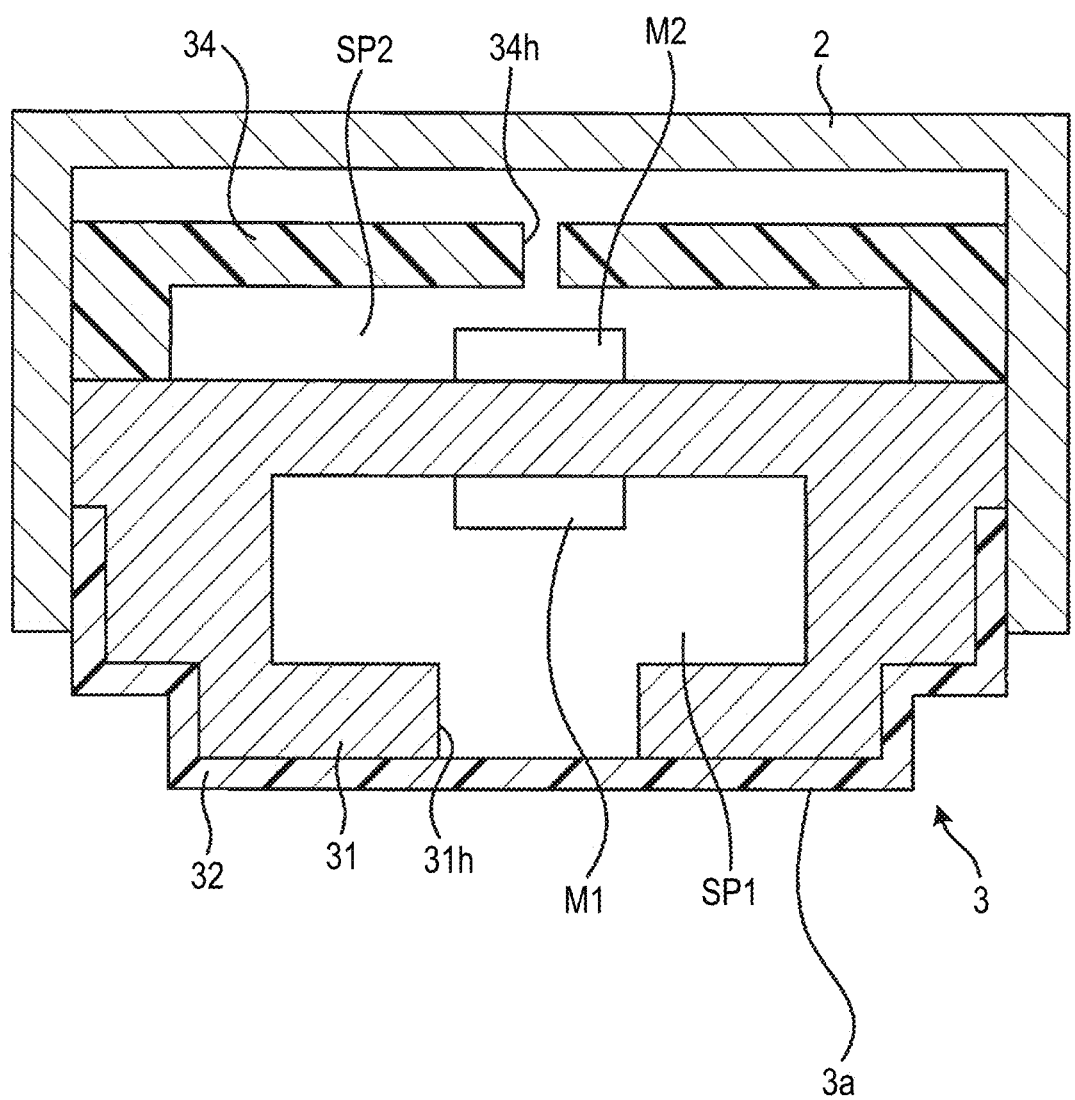
FIG. 2 is a schematic cross-sectional view of the wheezing detection device 1 taken along a line A-A in FIG. 1.

FIG. 2 is a schematic cross-sectional view of the wheezing detection device 1 taken along a line A-A in FIG. 1.

As illustrated in FIG. 2, the measurer 3 includes: a first sound measuring instrument M1 that measures a sound; a bottomed cylindrical first housing 31 which accommodates the first sound measuring instrument M1 in an accommodation space SP1 therein and which has an opening 31h that is blocked by a body surface S of a living body in a state where the first housing is pressed against the body surface S; a housing cover 32 that closes the opening 31h from an outer side of the first housing 31 and that covers the first housing 31; a second sound measuring instrument M2 that measures a sound; and a second housing 34 that forms an accommodation space SP2 for accommodating the second sound measuring instrument M2 and that has an opening 34h.

The measurer 3 is fitted into an opening portion formed in a housing 2 constituting the head portion 1a, with a part of the housing cover 32 being exposed, and is fixed to the housing 2.

A tip end portion of the part of the housing cover 32, which is exposed from the housing 2, is a flat surface or a curved surface, and this flat surface or curved surface constitutes the pressure receiving portion 3a. The housing 2 is made of resin or the like capable of transmitting a sound.

The first sound measuring instrument M1 is configured to measure a pulmonary sound, and is configured with, for example, a micro electro mechanical systems (MEMS) microphone or a capacitance-type microphone that measures a sound in a frequency band (for example, a frequency range of 10 Hz or more and 10 kHz or less) wider than a frequency range of pulmonary sound (generally, 10 Hz or more and 1 kHz or less). The first sound measuring instrument M1 functions as a sound measurer.

The first sound measuring instrument M1 is electrically connected to the integrated controller 4 illustrated in FIG. 1 by a lead wire (not illustrated) or the like, and transmits a signal of measured pulmonary sound to the integrated controller 4.

At the time of using the wheezing detection device 1, a state is established where the pressure receiving portion 3a of the housing cover 32 comes into contact with the body surface S and the accommodation space SP1 is sealed by the body surface S via the housing cover 32 under a pressure from the body surface S (hereinafter, this state is referred to as a sealed state).

Further, when the pressure receiving portion 3a vibrates due to the pulmonary sound transmitted from the living body to the body surface S, an internal pressure of the accommodation space SP1 fluctuates due to this vibration, and an electrical signal corresponding to the pulmonary sound is measured by the first sound measuring instrument M1 based on the fluctuation of the internal pressure.

The first housing 31 has a substantially convex shape directed in a lower direction in FIG. 2, and is made of a material having higher acoustic impedance than air and having high rigidity, such as a resin or a metal. The first housing 31 is made of a material that reflects a sound in a measurement frequency band of the first sound measuring instrument M1 so that the sound is not transmitted from the outside into the accommodation space SP1 in the sealed state.

The housing cover 32 is a bottomed cylindrical member, and a shape of a hollow portion thereof substantially coincides with a shape of an outer wall of the first housing 31.

The housing cover 32 is made of a material having acoustic impedance close to that of a human body, air, or water, and having flexibility and good biocompatibility. As a material of the housing cover 32, for example, silicon, an elastomer, or the like is used.

The second sound measuring instrument M2 is configured to measure an ambient sound of the first housing 31 (an environmental sound such as human speech, or a sound generated due to rubbing between the device and the living body or clothing), and is configured with, for example, an MEMS microphone or a capacitance-type microphone that measures a sound in a band (for example, a frequency range of 10 Hz or more and 10 kHz or less) wider than the frequency range of pulmonary sound.

The second sound measuring instrument M2 is electrically connected to the integrated controller 4 illustrated in FIG. 1 by a lead wire (not illustrated) or the like, and transmits a signal of a measured ambient sound to the integrated controller 4.

The second sound measuring instrument M2 is fixed to a surface of the first housing 31, opposite to the pressure receiving portion 3a side. A periphery of the second sound measuring instrument M2 is covered with the second housing 34. The second housing 34 is made of a material (for example, a resin) that allows a sound generated around the wheezing detection device 1 to easily enter the accommodation space SP2 for accommodating the second sound measuring instrument M2.

The opening 34h is formed in the second housing 34. Therefore, a structure is formed in which the sound generated around the wheezing detection device 1 easily enters from the opening 34h.

Figure 3:
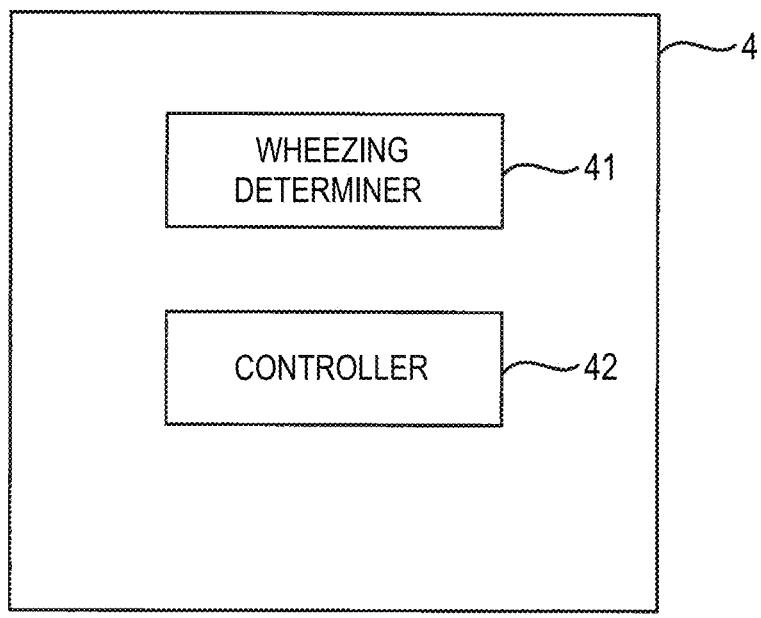
FIG. 3 is a functional block diagram of an integrated controller 4 shown in FIG. 1.

FIG. 3 is a functional block diagram of the integrated controller 4 shown in FIG. 1. A processor of the integrated controller 4 functions as a wheezing determiner 41 and a controller 42 by executing a wheezing detection program.

When an operating member 1c for instructing the start of wheezing detection processing, which is provided in the grip portion 1b, is operated and a start instruction of the wheezing detection processing is issued, in a state where the pressure receiving portion 3a is in contact with the body surface S of the subject, the wheezing determiner 41 sequentially acquires a signal of the pulmonary sound measured by the first sound measuring instrument M1 and an ambient sound signal measured by the second sound measuring instrument M2. Hereinafter, a timing at which a sound is first measured by the first sound measuring instrument M1 and the second sound measuring instrument M2 after the start instruction is issued is referred to as a measurement start time point.

The wheezing determiner 41 performs processing (hereinafter, referred to as "wheezing determination processing") of determining whether wheezing is included in the pulmonary sound of the subject, that is, determining presence or absence of wheezing, based on the signal of the pulmonary sound and the ambient sound signal that are sequentially acquired after the start instruction is issued.

For example, at a time point when a signal of the pulmonary sound and an ambient sound signal (referred to as a processing target signal group) are accumulated for a predetermined processing time period (for example, 1 second), the wheezing determiner 41 determines the presence or absence of wheezing based on the processing target signal group.

For example, the wheezing determiner 41 removes noise other than the pulmonary sound which is mixed in the signal of the pulmonary sound included in the processing target signal group, based on the ambient sound signal. Further, the wheezing determiner 41 determines presence or absence of wheezing based on a signal of the pulmonary sound subjected to noise removal.

The method of determining presence or absence of wheezing based on a signal of the pulmonary sound is not particularly limited, and for example, a method disclosed in Patent Literature 1 may be adopted. The wheezing determiner 41 performs such processing each time a new processing target signal group is accumulated, and determines presence or absence of wheezing for each processing time period.

In a case where an elapsed time period from the measurement start time point reaches a predetermined time period T1 set in advance, after the start instruction is issued, or in a case where it is determined by the wheezing determiner 41 that wheezing is included in the pulmonary sound of the subject, the controller 42 ends sound measurement performed by the first sound measuring instrument M1 and the second sound measuring instrument M2, and reports a result (wheezing is present or wheezing is absent) of the wheezing determination processing.

For example, the controller 42 causes the display unit 6 to display a message indicating the result of the wheezing determination processing, thereby reporting the result. A speaker may be installed in the wheezing detection device 1, and the report may be performed by outputting the message from the speaker.

The wheezing detection device 1 and an electronic device such as a smartphone may be configured to be able to communicate with each other. The message may be transmitted to the electronic device, and display or audio output of the message may be performed using a display or a speaker of the electronic device.

Alternatively, for example, a light emitting diode (LED) may be provided in the head portion 1a of the wheezing detection device 1, and the controller 42 may report the content by changing an emission color of the LED according to the result of the wheezing determination processing.

The predetermined time period T1 is a time period required for determining whether wheezing is included in the pulmonary sound. In order to determine presence or absence of wheezing, it is desirable to have a signal of the pulmonary sound of about 5 breaths.

Generally, the time required for 5 breaths at rest is 5 seconds to 10 seconds in a case of an infant under 6 in age, 13 seconds to 17 seconds in a case of a child at 6 or above and under 13 in age, 17 seconds to 25 seconds in a case of an adult at 13 or above and under 60 in age, and 10 seconds to 30 seconds in a case of an adult at 60 or above in age. Therefore, the predetermined time period T1 is a value selected from a range of 10 seconds or more and 30 seconds or less.

When a use target age of the wheezing detection device 1 is limited to, for example, being under 6, the predetermined time period T1 is preferably 10 seconds. When a use target age of the wheezing detection device 1 is limited to, for example, being under 13, the predetermined time period T1 is preferably 20 seconds. When a use target age of the wheezing detection device 1 is limited to, for example, being under 60, the predetermined time period T1 is preferably 25 seconds. When a use target age of the wheezing detection device 1 is not limited, the predetermined time period T1 is preferably 30 seconds. According to this configuration, the determination of presence or absence of wheezing can be performed targeting people of all ages. The wheezing detection device 1 is considered to be the most effective product for a child under 13 in age by whom alone it is difficult to determine a symptom of asthma.

(Operation Example of Wheezing Detection Device 1)

Figure 4:
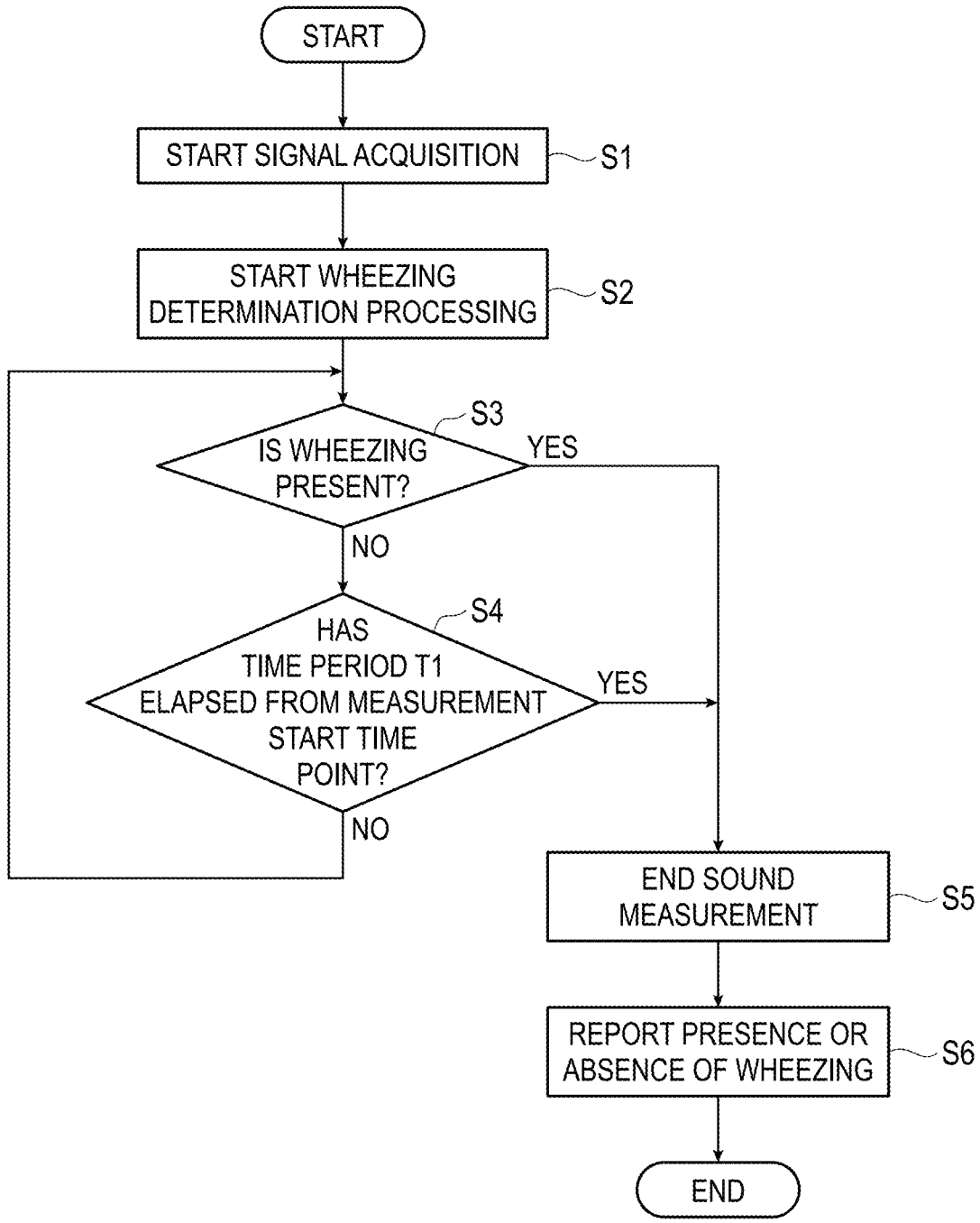
FIG. 4 is a flowchart for illustrating an operation example of the wheezing detection device 1.

FIG. 4 is a flowchart for illustrating an operation example of the wheezing detection device 1. When a start instruction of the wheezing detection processing is issued, the wheezing determiner 41 starts acquiring a signal of the pulmonary sound from the first sound measuring instrument M1 and acquiring an ambient sound signal from the second sound measuring instrument M2 (step S1).

Further, the wheezing determiner 41 starts wheezing determination processing based on the acquired signal of the pulmonary sound and the ambient sound signal (step S2).

When the wheezing determination processing is started, the controller 42 determines whether it is determined by the wheezing determiner 41 to be "wheezing is present" (step S3).

When it is determined to be "wheezing is present" (step S3: YES), the controller 42 ends sound measurement performed by the first sound measuring instrument M1 and the second sound measuring instrument M2 (step S5). Further, the controller 42 reports a result (here, "wheezing is present") of the wheezing determination processing (step S6).

On the other hand, when it is not determined to be "wheezing is present" (step S3: NO), the controller 42 determines whether an elapsed time period from the measurement start time point reaches the predetermined time period T1 (step S4). When it is determined that the elapsed time period has not reached the predetermined time period T1 (step S4: NO), the controller 42 returns the process to step S3.

When the elapsed time period reaches the predetermined time period T1 (step S4: YES), the controller 42 ends the sound measurement performed by the first sound measuring instrument M1 and the second sound measuring instrument M2 in step S5, and in step S6, reports a result of the wheezing determination processing performed by the wheezing determiner 41.

At a time point when the elapsed time period reaches the predetermined time period T1, the wheezing determiner 41 may still be performing the wheezing determination processing. In such a case, when it is determined to be "wheezing is present" in any of wheezing determination processes terminated after this time point, the result of "wheezing is present" is reported in step S6. On the other hand, when it is determined to be "wheezing is absent" in the wheezing determination processes, a result of "wheezing is absent" is reported in step 6. In a case where the wheezing determination processing performed by the wheezing determiner 41 has ended at the time point when the elapsed time period reaches the predetermined time period T1, a result of "wheezing is absent" is reported in step S6.

(Effects of Wheezing Detection Device 1)

As described above, according to the wheezing detection device 1, when it is determined that wheezing is included in the pulmonary sound of the subject after the start instruction is issued, the pulmonary sound measurement is ended, and the result of "wheezing is present" is reported. Therefore, in a case of a subject in which wheezing is frequently occurring, it is possible to know early that wheezing has occurred, and it is possible to improve convenience. In addition, the subject does not have to be kept at rest for a long time, and the burden on both the subject and a user can be reduced. Further, the pulmonary sound measurement can be terminated early, and power consumption can be reduced.

When the elapsed time period from the measurement start time point reaches the predetermined time period T1, the pulmonary sound measurement is ended, and the result of the processing performed by the wheezing determiner 41 is reported. Since the predetermined time period T1 is a time period required for determining presence or absence of wheezing, when the elapsed time period reaches the predetermined time period T1, the result of presence or absence of wheezing can be obtained with high reliability. The user may only continue the use of the device until the result is reported without paying particular attention to the predetermined time period T1. Therefore, the convenience of the device can be improved. In other words, according to the present invention, it is possible to provide a wheezing detection device and a wheezing detection program capable of shortening a time period to an end of use of the device in some cases while ensuring a sufficient amount of signal of pulmonary sound to determine presence or absence of wheezing.

(Modification of Wheezing Detection Device 1)

Hereinafter, modifications of the wheezing detection device 1 will be described.

<First Modification>

Figure 5:
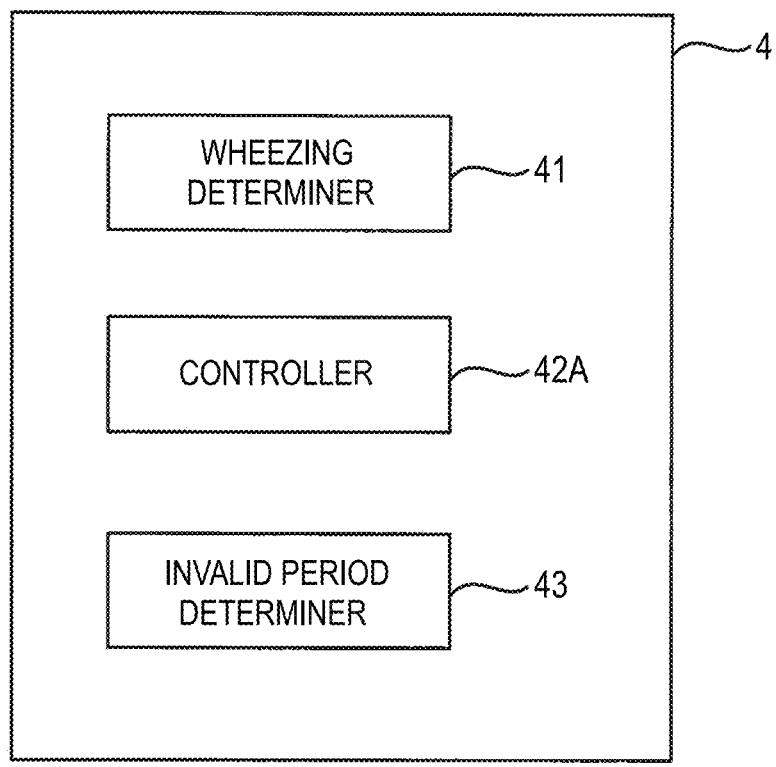
FIG. 5 is a diagram illustrating a modification of a functional block of the integrated controller 4 of the wheezing detection device 1.

FIG. 5 is a diagram illustrating a modification of a functional block of the integrated controller 4 of the wheezing detection device 1. In FIG. 5, a block having the same function as that in FIG. 3 is denoted by the same reference sign. A processor of the integrated controller 4 shown in FIG. 5 functions as the wheezing determiner 41, a controller 42A, and an invalid period determiner 43 by executing a wheezing detection program.

The invalid period determiner 43 determines whether a signal of the pulmonary sound, which is measured by the first sound measuring instrument M1 and acquired by the wheezing determiner 41, is a specific signal, and when the signal is determined to be a specific signal, determines a period (between a measurement time point of the signal and a measurement time point of a signal immediately before the signal) in which the signal is measured as an invalid period. A length of this period corresponds to a sampling interval of the signal of the pulmonary sound.

The specific signal described above refers to a signal that may affect a result of the wheezing determination processing performed by the wheezing determiner 41, and specifically, a signal including a large amount of noise other than a pulmonary sound. Examples of method for determining whether a signal of the pulmonary sound is a specific signal include, but are not limited to, the following three methods (A) to (C).

(A) When a level of an ambient sound signal, which is measured by the second sound measuring instrument M2 at the same time as a signal of the pulmonary sound, is equal to or greater than a threshold, it is determined that the signal of the pulmonary sound is a specific signal; when the level of the ambient sound signal is less than the threshold, it is determined that the signal of the pulmonary sound is not a specific signal.

(B) A contact sensor for detecting contact with an object is provided in the pressure receiving portion 3a, and a contact state (whether the pressure receiving portion 3a is in a sealed state) of the pressure receiving portion 3a with respect to the body surface S at a time point when a signal of the pulmonary sound is measured is determined based on detection information of the contact sensor. Further, when the pressure receiving portion 3a is separated from the body surface S and the sealed state cannot be secured, it is determined that the signal of the pulmonary sound is a specific signal, and when the pressure receiving portion 3a is in contact with the body surface S and the sealed state is secured, it is determined that the signal of the pulmonary sound is not a specific signal.

(C) An acceleration sensor is provided in the wheezing detection device 1, and a motion amount of the device between a time point when a signal of the pulmonary sound is measured and another time point, immediately before the time point, when a signal of the pulmonary sound is measured is obtained based on detection information of the acceleration sensor. When the motion amount is large, it is determined that the signal is a specific signal, and when the motion amount is small, it is determined that the signal is not a specific signal.

In a case where an elapsed time period from the measurement start time point reaches a predetermined time period T2 set in advance, after a start instruction is issued, or in a case where it is determined by the wheezing determiner 41 that wheezing is included in the pulmonary sound of a subject, the controller 42A ends sound measurement performed by the first sound measuring instrument M1 and the second sound measuring instrument M2, and reports a result of the wheezing determination processing.

In a case where total time of periods determined as invalid periods by the invalid period determiner 43 exceeds a predetermined threshold TH1 after the start instruction is issued, the controller 42A ends the sound measurement performed by the first sound measuring instrument M1 and the second sound measuring instrument M2, and reports a state where determination of presence or absence of wheezing is not possible. A reporting method used by the controller 42A is the same as a reporting method used by the controller 42.

The predetermined time period T2 is a time period obtained by adding a time period determined in consideration of occurrence of the invalid period to the time period (predetermined time period T1 described above) required for determining whether wheezing is included in a pulmonary sound. Specifically, the predetermined time period T2 is preferably set to a value about twice the predetermined time period T1.

That is, the predetermined time period T2 is preferably a value selected from a range of 20 seconds or more and 60 seconds or less. When the predetermined time period T2 is twice the predetermined time period T1, a value of half the predetermined time period T2 is set as the threshold TH1. According to this configuration, the determination of presence or absence of wheezing performed by the wheezing determiner can be performed with sufficient accuracy.

When a use target age of the wheezing detection device 1 is limited to, for example, being under 6, the predetermined time period T2 is preferably 20 seconds and the threshold TH1 is preferably 10 seconds. When a use target age of the wheezing detection device 1 is limited to, for example, being under 13, the predetermined time period T2 is preferably 40 seconds and the threshold TH1 is preferably 20 seconds. According to this configuration, determination of presence or absence of wheezing can be performed targeting an infant or a school child. Further, when a use target age of the wheezing detection device 1 is limited to, for example, being under 60, the predetermined time period T2 is preferably 50 seconds and the threshold TH1 is preferably 25 seconds. When a use target age of the wheezing detection device 1 is not limited, the predetermined time period T2 is preferably 60 seconds and the threshold TH1 is preferably 30 seconds. According to this configuration, determination of presence or absence of wheezing can be performed targeting people of all ages.

Figure 6:
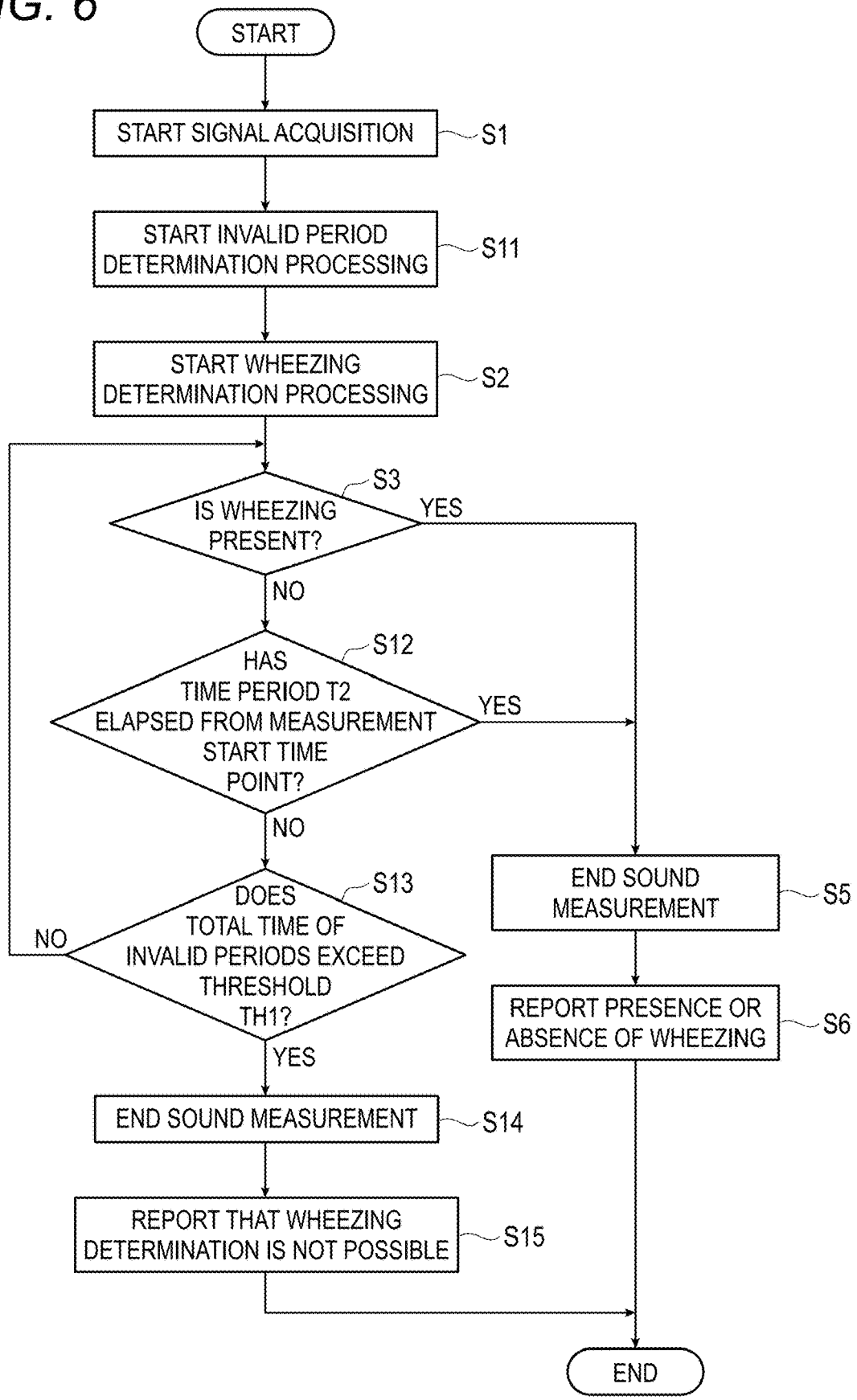
FIG. 6 is a flowchart for illustrating an operation example of a wheezing detection device 1 including the integrated controller 4 shown in FIG. 5.

FIG. 6 is a flowchart for illustrating an operation example of a wheezing detection device 1 including the integrated controller 4 shown in FIG. 5. In FIG. 6, the same processes as those in FIG. 4 are denoted by the same reference signs, and descriptions thereof are omitted.

When signal acquisition is started in step S1, the invalid period determiner 43 starts determining whether a period in which a signal of the pulmonary sound acquired in step S1 is measured is an invalid period (step S11). When the signal acquisition is started in step S1, the wheezing determination processing is started in step S2.

When it is not determined to be "wheezing is present" in step S3 (step S3: NO), the controller 42A determines whether an elapsed time period from the measurement start time point reaches the predetermined time period T2 (step S12). When it is determined that the elapsed time period reaches the predetermined time period T2 (step S12: YES), processing of step S5 and step S6 is performed.

When the elapsed time period has not reached the predetermined time period T2 (step S12: NO), the controller 42A calculates total time of periods determined as invalid periods by the invalid period determiner 43, and determines whether the total time exceeds the threshold TH1 (step S13).

When the total time is equal to or less than threshold TH1 (step S13: NO), the controller 42A returns the process to step S3.

When the total time exceeds the threshold TH1 (step S13: YES), the controller 42A ends the sound measurement performed by the first sound measuring instrument M1 and the second sound measuring instrument M2 (step S14). Further, the controller 42A reports that determination of presence or absence of wheezing is not possible (step S15).

At a time point when the elapsed time period reaches the predetermined time period T2 (step S12: YES), the wheezing determiner 41 may still be performing the wheezing determination processing. In such a case, when it is determined to be "wheezing is present" in any of wheezing determination processes terminated after this time point, a result of "wheezing is present" is reported in step S6. On the other hand, when it is determined to be "wheezing is absent" in the wheezing determination processes, a result of "wheezing is absent" is reported in step 6. In a case where the wheezing determination processing performed by the wheezing determiner 41 has ended at the time point when the elapsed time period reaches the predetermined time period T2, a result of "wheezing is absent" is reported in step S6.

(Effects of First Modification)

According to the first modification, when the total time of the periods determined as the invalid periods exceeds the threshold TH1 with respect to the predetermined time period T2, which is a maximum value of a time period in which the pulmonary sound is measured after the start instruction, a state where the determination of presence or absence of wheezing is not possible is reported.

In a state where the total time exceeds the threshold TH1, a signal of the pulmonary sound having high reliability is acquired for a time period less than the above-mentioned predetermined time period T1, at the time point when the elapsed time period from the measurement start time point reaches the predetermined time period T2.

Therefore, in such a case, by reporting a state where the determination of presence or absence of wheezing is not possible, it is possible to prevent a result of the processing performed by the wheezing determiner 41 from being reported in a state where the reliability is low.

In other words, since the result of the processing performed by the wheezing determiner 41 can be reported only in a state where it can be determined that the reliability is high, reliability of the device can be improved. In addition, when the total time of the invalid periods exceeds the threshold TH1, the sound measurement performed by the first sound measuring instrument M1 and the second sound measuring instrument M2 is ended at that time point. Therefore, unnecessary sound measurement can be eliminated, and power consumption of the device can be reduced.

<Second Modification>

Figure 7:
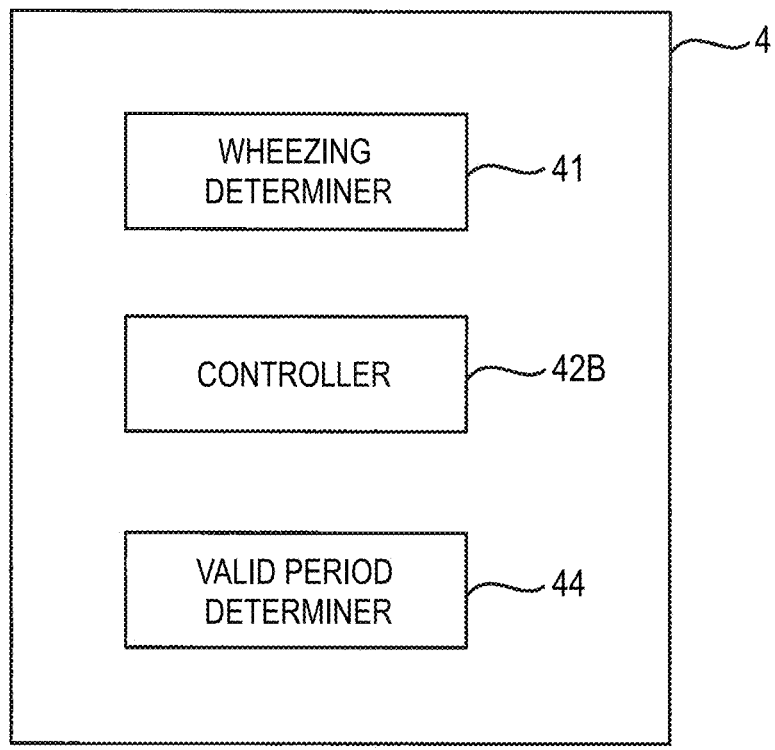
FIG. 7 is a diagram illustrating a modification of the functional block of the integrated controller 4 of the wheezing detection device 1.

FIG. 7 is a diagram illustrating a modification of the functional block of the integrated controller 4 of the wheezing detection device 1. In FIG. 7, a block having the same function as that in FIG. 3 is denoted by the same reference sign. A processor of the integrated controller 4 shown in FIG. 7 functions as the wheezing determiner 41, a controller 42B, and a valid period determiner 44 by executing a wheezing detection program.

The valid period determiner 44 determines whether a signal of the pulmonary sound, which is measured by the first sound measuring instrument M1 and acquired by the wheezing determiner 41, is a specific signal described above, and when the signal is not determined to be a specific signal, determines a period (between a measurement time point of the signal and a measurement time point of a signal immediately before the signal) in which the signal is measured as a valid period. A length of this period corresponds to a sampling interval of the signal of the pulmonary sound.

In a case where after a start instruction is issued, total time of periods determined as valid periods by the valid period determiner 44 after the start instruction is issued reaches the predetermined time period T1, or in a case where it is determined by the wheezing determiner 41 that wheezing is included in the pulmonary sound of a subject, the controller 42B ends sound measurement performed by the first sound measuring instrument M1 and the second sound measuring instrument M2, and reports a result of the wheezing determination processing.

Figure 8:
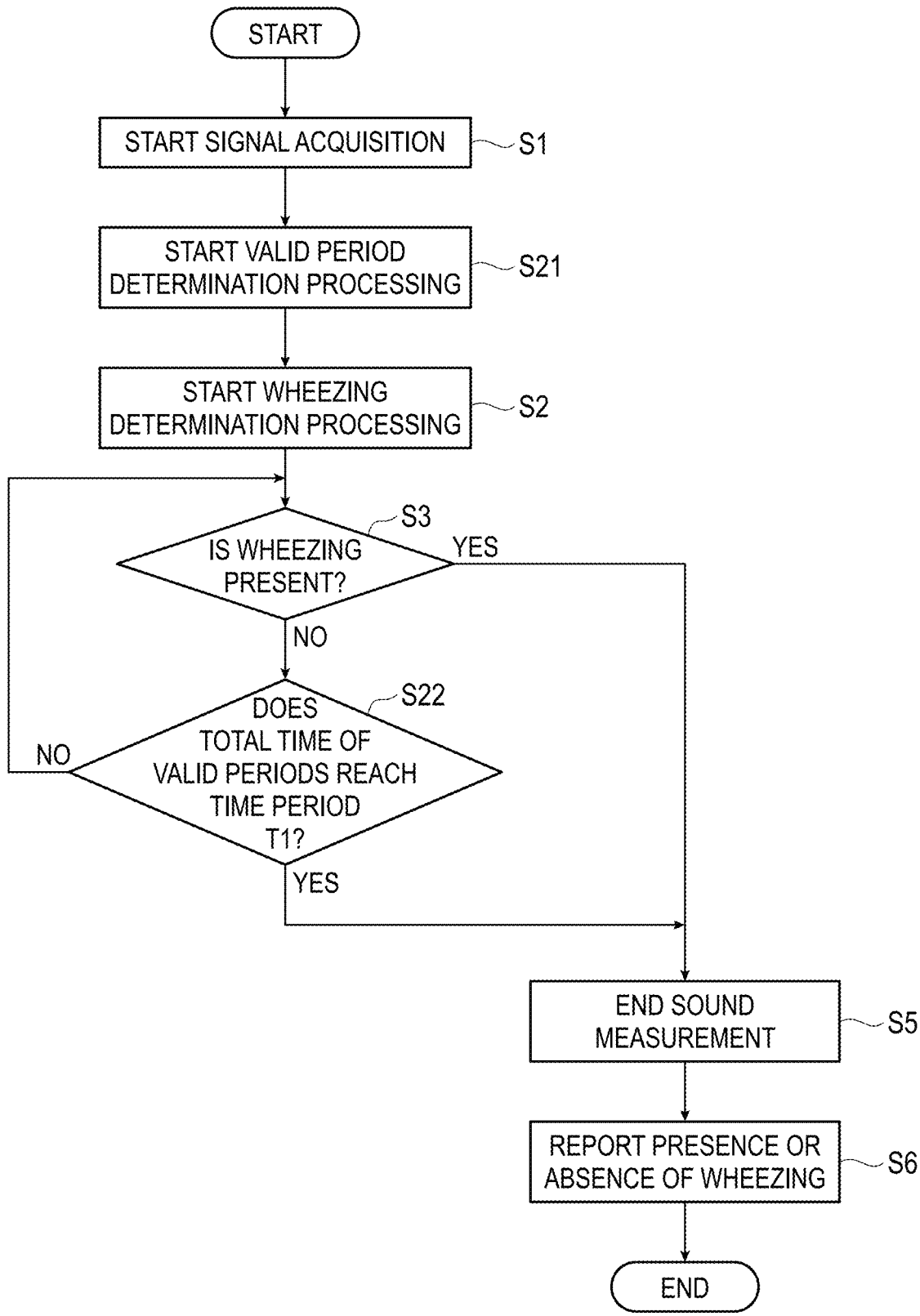
FIG. 8 is a flowchart for illustrating an operation example of a wheezing detection device 1 including the integrated controller 4 shown in FIG. 7.

FIG. 8 is a flowchart for illustrating an operation example of a wheezing detection device 1 including the integrated controller 4 shown in FIG. 7. In FIG. 8, the same processes as those in FIG. 4 are denoted by the same reference signs, and descriptions thereof are omitted. When signal acquisition is started in step S1, the valid period determiner 44 starts determining whether a period in which a signal of the pulmonary sound acquired in step S1 is measured is a valid period (step S21). When the signal acquisition is started in step S1, the wheezing determination processing is started in step S2.

When it is not determined to be "wheezing is present" in step S3 (step S3: NO), the controller 42B calculates total time of periods determined as valid periods by the valid period determiner 44, and determines whether the total time reaches the predetermined time period T1 (step S22).

When the total time is less than the predetermined time period T1 (step S22: NO), the controller 42B returns the process to step S3.

When the total time reaches the predetermined time period T1 (step S22: YES), the controller 42B ends sound measurement performed by the first sound measuring instrument M1 and the second sound measuring instrument M2 in step S5, and reports a result of the wheezing determination processing in step S6.

At a time point when the total time reaches the predetermined time period T1, the wheezing determiner 41 may still be performing the wheezing determination processing. In such a case, when it is determined to be "wheezing is present" in any of wheezing determination processes terminated after this time point, a result of "wheezing is present" is reported in step S6. On the other hand, when it is determined to be "wheezing is absent" in the wheezing determination processes, a result of "wheezing is absent" is reported in step S6. In a case where the wheezing determination processing performed by the wheezing determiner 41 has ended at the time point when the total time reaches the predetermined time period T1, a result of "wheezing is absent" is reported in step S6.

(Effects of Second Modification)

According to the second modification, when it is determined that wheezing is included in the pulmonary sound of the subject (step S3: YES), the pulmonary sound measurement is terminated, and the result that wheezing is included is reported. Therefore, in a case of a subject in which wheezing is frequently occurring, a user of the device can know early that wheezing has occurred, and the convenience can be improved. In addition, the subject does not have to be kept at rest for a long time, and the burden on both the subject and the user can be reduced. Further, the pulmonary sound measurement can be terminated early, and power consumption can be reduced.

When the total time of the periods determined as the valid periods reaches the predetermined time period T1, the pulmonary sound measurement is ended, and the result of determination of presence or absence of wheezing is reported. Since the predetermined time period T1 is a time period required for determining presence or absence of wheezing, when the total time reaches the predetermined time period T1, the result of determination of presence or absence of wheezing can be obtained with high reliability. The user may only continue the use of the device until the result is reported without paying particular attention to the predetermined time period T1. Therefore, the convenience of the device can be improved.

<Third Modification>

Figure 9:
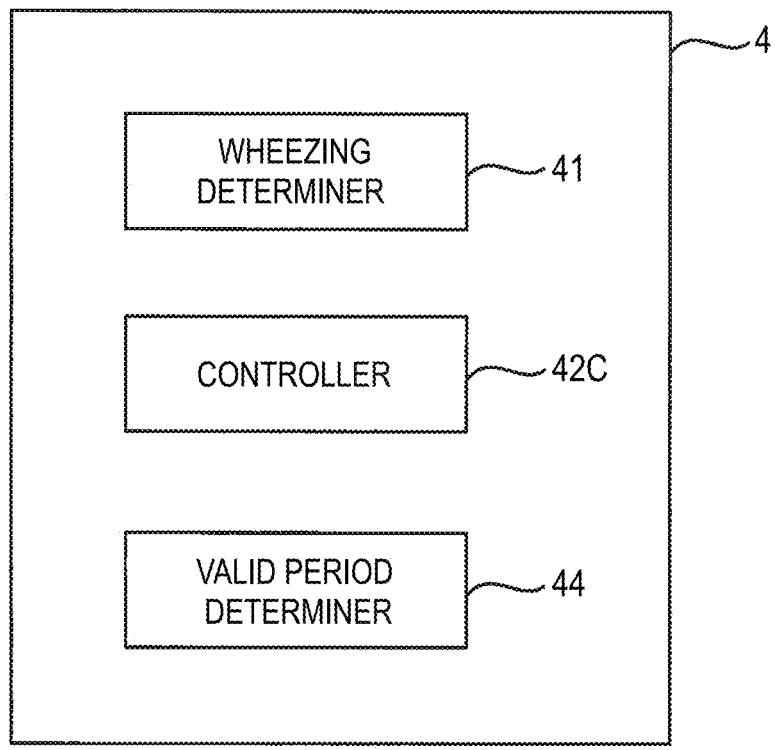
FIG. 9 is a diagram illustrating a modification of the functional block of the integrated controller 4 of the wheezing detection device 1.

FIG. 9 is a diagram illustrating a modification of the functional block of the integrated controller 4 of the wheezing detection device 1. In FIG. 9, a block having the same function as that in FIG. 7 is denoted by the same reference sign. A processor of the integrated controller 4 shown in FIG. 9 functions as the wheezing determiner 41, a controller 42C, and the valid period determiner 44 by executing a wheezing detection program.

The controller 42C selectively performs control (referred to as a first control) performed by the controller 42 shown in FIG. 3, control (referred to as a third control) performed by the controller 42A shown in FIG. 5, and control (referred to as a second control) performed by the controller 42B shown in FIG. 7. The controller 42C determines which control is to be performed in accordance with a mode designated by an operation of a mode switching button or the like provided in the device.

The first control is control of ending sound measurement performed by the first sound measuring instrument M1 and the second sound measuring instrument M2 and reporting a result of the wheezing determination processing, in a case where an elapsed time period from the measurement start time point reaches the predetermined time period T1 set in advance, or in a case where it is determined by the wheezing determiner 41 that wheezing is included in the pulmonary sound of a subject.

The third control is control of ending sound measurement performed by the first sound measuring instrument M1 and the second sound measuring instrument M2 and reporting a result of the wheezing determination processing, in a case where an elapsed time period from the measurement start time point reaches the predetermined time period T2 set in advance, or in a case where it is determined by the wheezing determiner 41 that wheezing is included in the pulmonary sound of a subject. In addition, the third control is control of ending sound measurement performed by the first sound measuring instrument M1 and the second sound measuring instrument M2 and reporting that wheezing determination is not possible, in a case where total time of invalid periods exceeds the threshold TH1 in a process in which an elapsed time period from the measurement start time point reaches the predetermined time period T2.

The second control is control of ending sound measurement performed by the first sound measuring instrument M1 and the second sound measuring instrument M2 and reporting a result of the wheezing determination processing, in a case where total time of periods determined as valid periods by the valid period determiner 44 after a start instruction is issued reaches the predetermined time period T1, or in a case where it is determined by the wheezing determiner 41 that wheezing is included in the pulmonary sound of a subject.

Operations of the wheezing detection device 1 including the integrated controller 4 shown in FIG. 9 are those illustrated in FIG. 4 when a mode for performing the first control is designated, those illustrated in FIG. 6 when a mode for performing the third control is designated, and those illustrated in FIG. 8 when a mode for performing the second control is designated. In addition, there may be a mode in which any two of the first control, the second control, and the third control are performed in parallel.

According to the third modification described above, for example, proper use of the device is possible, that is, the device can be operated in a mode for performing the first control when a result of the wheezing determination processing is desired to be obtained in a short time, or the device can be operated in a mode for performing the second control or the third control when a result of the wheezing determination processing is desired to be obtained with high accuracy. Therefore, the convenience of the device can be improved.

<Other Modifications>

A contact sensor may be provided in the pressure receiving portion 3a, and during operations illustrated in FIG. 4, FIG. 6 or FIG. 8, the integrated controller 4 may determine a close contact state of the pressure receiving portion 3a with respect to the body surface S based on information of the contact sensor. When the close contact state does not satisfy a measurement condition, the integrated controller 4 may end measurement of a pulmonary sound and an ambient sound and report that determination of presence or absence of wheezing is not possible.

Functions of the integrated controller 4 may be provided in an electronic device such as a smartphone, and the measurer 3 may be detachably attached to the electronic device. That is, a processor of the electronic device may function as the integrated controller 4 by executing a wheezing detection program.

The second sound measuring instrument M2 is not essential and may be omitted. The measurer 3 may not have the structure shown in FIG. 2 as long as the first sound measuring instrument M1 can measure a pulmonary sound.

Although the embodiments are described above with reference to the drawings, it is needless to say that the present invention is not limited to such examples. It will be apparent to those skilled in the art that various changes and modifications may be conceived within the scope of the claims. It is also understood that the various changes and modifications belong to the technical scope of the present invention. Components in the embodiments described above may be combined freely within a range not departing from the spirit of the present invention.

What is claimed is:

1. A wheezing detection device, comprising:
a head portion;
a grip portion including an operating member;
a display;
a housing including a pressure receiving portion and a microphone on the head portion and configured to measure a pulmonary sound of a subject;
one or more processors and memories configured or programmed to function as:
a wheezing determiner to perform processing of determining whether wheezing is included in the pulmonary sound of the subject based on the pulmonary sound that is measured by the microphone after the operating member on the wheezing detection device is operated by a user to issue an instruction for starting wheezing detection processing; and
a controller to end measurement of the pulmonary sound performed by the microphone and report a result of the processing via the display, in a first case where an elapsed time period from a measurement start time point of the pulmonary sound, which is firstly measured by the microphone after the instruction is issued, reaches a predetermined time period set in advance, or in a second case where the wheezing determiner determines that wheezing is included in the pulmonary sound of the subject.

2. The wheezing detection device according to claim 1, wherein the one or more processors and memories are further configured or programmed to function as:
an invalid period determiner to determine whether the pulmonary sound measured by the microphone includes a specific sound possible to affect a result of the processing, and that when the pulmonary sound is determined to include the specific sound, determine one or more periods in which the pulmonary sound is measured as an invalid period, and
the controller further ends the measurement of the pulmonary sound performed by the microphone and reports a state where determination of presence or absence of wheezing is not possible where a total time of the one or more periods determined as the invalid period exceeds a predetermined threshold.

3. The wheezing detection device according to claim 2, wherein the predetermined time period is a time period selected from a range greater than or equal to 20 seconds and less than or equal to 60 seconds.

4. The wheezing detection device according to claim 3, wherein the predetermined time period is a time period selected from a range greater than or equal to 20 seconds and less than or equal to 40 seconds.

5. The wheezing detection device according to claim 3, wherein the threshold is a value of half of the predetermined time period.

6. The wheezing detection device according to claim 1, wherein the predetermined time period is a time period selected from a range greater than or equal to 10 seconds and less than or equal to 30 seconds.

7. A wheezing detection device, comprising:
a head portion;
a grip portion including an operating member;
a display;
a housing including a pressure receiving portion and a microphone on the head portion and configured to measure a pulmonary sound of a subject; and
one or more processors and memories configured or programmed to function as:
a wheezing determiner to perform processing of determining whether wheezing is included in the pulmonary sound of the subject based on the pulmonary sound that is measured by the microphone after the operating member on the wheezing detection device is operated by a user to issue an instruction for starting wheezing detection processing;
a valid period determiner to determine whether the pulmonary sound measured by the microphone includes a specific sound possible to affect a result of the processing, and that when the pulmonary sound is not determined to include the specific sound, determine one or more periods in which the pulmonary sound is measured as a valid period; and
a controller to end measurement of the pulmonary sound performed by the microphone and report a result of the processing via the display, in a first case where a total time of the one or more periods determined as the valid period after the instruction is issued reaches a predetermined time period set in advance, or in a second case where the wheezing determiner determines that wheezing is included in the pulmonary sound of the subject.

8. The wheezing detection device according to claim 7, wherein the predetermined time period is a time period selected from a range greater than or equal to 10 seconds and less than or equal to 30 seconds.

9. A wheezing detection device, comprising:
a head portion;
a grip portion including an operating member;
a display;
a housing including a pressure receiving portion and a microphone on the head portion to measure a pulmonary sound of a subject; and
one or more processors and memories configured or programmed to function as:
a wheezing determiner to perform processing of determining whether wheezing is included in the pulmonary sound of the subject based on the pulmonary sound that is measured by the microphone after the operating member on the wheezing detection device is operated by a user to issue an instruction for starting wheezing detection processing;
a valid period determiner to determine whether the pulmonary sound measured by the microphone includes a specific sound possible to affect a result of the processing, and that when the pulmonary sound is not determined to include the specific sound, determine one or more periods in which the pulmonary sound is measured as a valid period;

an invalid period determiner to determine whether the pulmonary sound measured by the microphone includes a specific sound possible to affect a result of the processing, and that when the pulmonary sound is determined to be the specific sound, determine one or more periods in which the pulmonary sound is measured as an invalid period; and a controller to selectively perform one or two of a first control, a second control, and a third control, wherein the first control is a control of ending measurement of the pulmonary sound performed by the microphone and reporting a result of the processing via the display, in a first case where an elapsed time period from a measurement start time point of the pulmonary sound, which is firstly measured by the microphone after the instruction is issued, reaches a predetermined time period set in advance, or in a second case where the wheezing determiner determines that wheezing is included in the pulmonary sound of the subject, wherein the third control is a control of ending measurement of the pulmonary sound performed by the microphone and reporting a result of the processing via the display, in a third case where an elapsed time period from a measurement start time point of the pulmonary sound, which is firstly measured by the microphone after the instruction is issued, reaches a predetermined time period set in advance, or in a fourth case where the wheezing determiner determines that wheezing is included in the pulmonary sound of the subject, and further ending the measurement of the pulmonary sound performed by the microphone and reporting a state where determination of presence or absence of wheezing is not possible via the display, in a fifth case where a total time of the one or more periods determined as the invalid time period exceeds a predetermined threshold when the elapsed time period reaches the predetermined time period, and wherein the second control is a control of ending measurement of the pulmonary sound performed by the microphone and reporting a result of the processing via the display, in a seventh case where a total time of the one or more periods determined as the valid period after the instruction is issued reaches a predetermined time period set in advance, or in an eighth case where the wheezing determiner determines that wheezing is included in the pulmonary sound of the subject.

10. A non-transitory computer readable storage medium which stores a wheezing detection program for causing a computer to execute:

a wheezing determining step of performing processing of determining whether wheezing is included in a pulmonary sound of a subject, based on the pulmonary sound that is measured, by a microphone configured to measure the pulmonary sound of the subject, after an operating member on a wheezing detection device is operated by a user to issue an instruction for starting wheezing detection processing; and a control step of ending measurement of the pulmonary sound performed by the microphone and reporting a result of the processing via a display of the wheezing detection device, in a first case where an elapsed time period from a measurement start time point of the pulmonary sound, which is firstly measured by the microphone after the instruction is issued, reaches a predetermined time period set in advance, or in a second case where the wheezing determining step determines that wheezing is included in the pulmonary sound of the subject.

11. A non-transitory computer readable storage medium which stores a wheezing detection program for causing a computer to execute:

a wheezing determining step of performing processing of determining whether wheezing is included in a pulmonary sound of a subject, based on the pulmonary sound that is measured, by a microphone configured to measure the pulmonary sound of the subject, after an operating member on a wheezing detection device is operated by a user to issue an instruction for starting wheezing detection processing;

a valid period determining step of determining whether the pulmonary sound measured by the microphone includes a specific sound possible to affect a result of the processing, and when the pulmonary sound is not determined to include the specific sound, determining one or more periods in which the pulmonary sound is measured as a valid period; and a control step of ending measurement of the pulmonary sound performed by the microphone and reporting a result of the processing via a display of the wheezing detection device, in a first case where a total time of the one or more periods determined as the valid period after the instruction is issued reaches a predetermined time period set in advance, or in a second case where the wheezing determining step determines that wheezing is included in the pulmonary sound of the subject.

12. A non-transitory computer readable storage medium which stores a wheezing detection program for causing a computer to execute:

a wheezing determining step of performing processing of determining whether wheezing is included in a pulmonary sound of a subject, based on the pulmonary sound that is measured, by a microphone configured to measure the pulmonary sound of the subject, after an operating member on a wheezing detection device is operated by a user to issue an instruction for starting wheezing detection processing;

a valid period determining step of determining whether the pulmonary sound measured by the microphone includes a specific sound possible to affect a result of the processing, and when the pulmonary sound is not determined to include the specific sound, determining one or more periods in which the pulmonary sound is measured as a valid period;

an invalid period determining step of determining whether the pulmonary sound measured by the microphone includes the specific sound possible to affect a result of the processing, and when the pulmonary sound is determined to include the specific sound, determining one or more periods in which the pulmonary sound is measured as an invalid period; and a control step of selectively performing one or two of a first control, a second control, and a third control, wherein the first control is a control of ending measurement of the pulmonary sound performed by the microphone and reporting a result of the processing via a display of the wheezing detection device, in a first case where an elapsed time period from a measurement start time point of the pulmonary sound, which is firstly measured by the microphone after the instruction is issued, reaches a predetermined time period set in advance, or in a second case where the wheezing determining step determines that wheezing is included in the pulmonary sound of the subject, wherein the third control is a control of ending measurement of the signal of the pulmonary sound performed by the microphone and reporting a result of the processing via the display, in a third case where an elapsed time period from a measurement start time point of the signal, which is firstly measured by the microphone after the instruction is issued, reaches a predetermined time period set in advance, or in a fourth case where the wheezing determining step determines that wheezing is included in the pulmonary sound of the subject, and further ending the measurement of the pulmonary sound performed by the microphone and reporting a state where determination of presence or absence of wheezing is not possible via the display, in a fifth case where a total time of the one or more periods determined as the invalid time period exceeds a predetermined threshold when the elapsed time period reaches the predetermined time period, and wherein the second control is a control of ending measurement of the pulmonary sound performed by the microphone and reporting a result of the processing via the display, in a sixth case where a total time of the one or more periods determined as the valid period after the instruction is issued reaches a predetermined time period set in advance, or in a seventh case where the wheezing determining step determines that wheezing is included in the pulmonary sound of the subject.

* * * * *